United States Patent [19]

Mann et al.

[11] 4,082,097

[45] Apr. 4, 1978

[54] MULTIMODE RECHARGING SYSTEM FOR LIVING TISSUE STIMULATORS

[75] Inventors: Alfred E. Mann; Joseph H. Schulman, both of Los Angeles, Calif.

[73] Assignee: Pacesetter Systems Inc., Sylmar, Calif.

[21] Appl. No.: 688,411

[22] Filed: May 20, 1976

[51] Int. Cl.² .................................. A61N 1/36
[52] U.S. Cl. ............................. 128/419 PS; 320/32; 320/46; 320/48
[58] Field of Search .................. 128/419 PS, 419 PT; 320/28, 29, 31, 30, 32, 33, 43, 34, 46, 45, 48

[56] References Cited

U.S. PATENT DOCUMENTS

| 1,034,108 | 7/1912 | Halbleib | 320/46 |
| 2,104,632 | 1/1938 | Agnew | 320/46 X |
| 2,885,623 | 5/1959 | Staufenberg, Jr. | 320/29 X |
| 3,477,009 | 11/1969 | Nichols | 320/46 X |
| 3,621,359 | 11/1971 | Schnegg | 320/48 X |
| 3,652,915 | 3/1972 | Eberts | 320/46 X |
| 3,867,681 | 2/1975 | Bishop et al. | 320/31 X |
| 3,888,260 | 6/1975 | Fischell | 128/419 PS |
| 3,946,299 | 3/1976 | Christianson et al. | 320/43 |

Primary Examiner—William E. Kamm
Attorney, Agent, or Firm—Lindenberg, Freilich, Hornbaker, Wasserman, Rosen & Fernandez

[57] ABSTRACT

A system is disclosed for controlling the charging of a rechargeable battery in an implanted human tissue stimulator by means of an external power source. Included in the stimulator are battery protection devices designed to sense the state of charge of the battery and limit the charging current amplitude so as not to exceed a selected maximum based on different criteria including battery state of charge signals from the implanted stimulator which are indicative of the current amplitude and battery state of charge from one of the protection devices are transmited to an external unit. Based on these signals the external unit is operated in one of a plurality of modes to cause the battery to be charged by a current with an optimum safe amplitude irrespective of determined failure of one or more of the battery protection devices.

16 Claims, 8 Drawing Figures

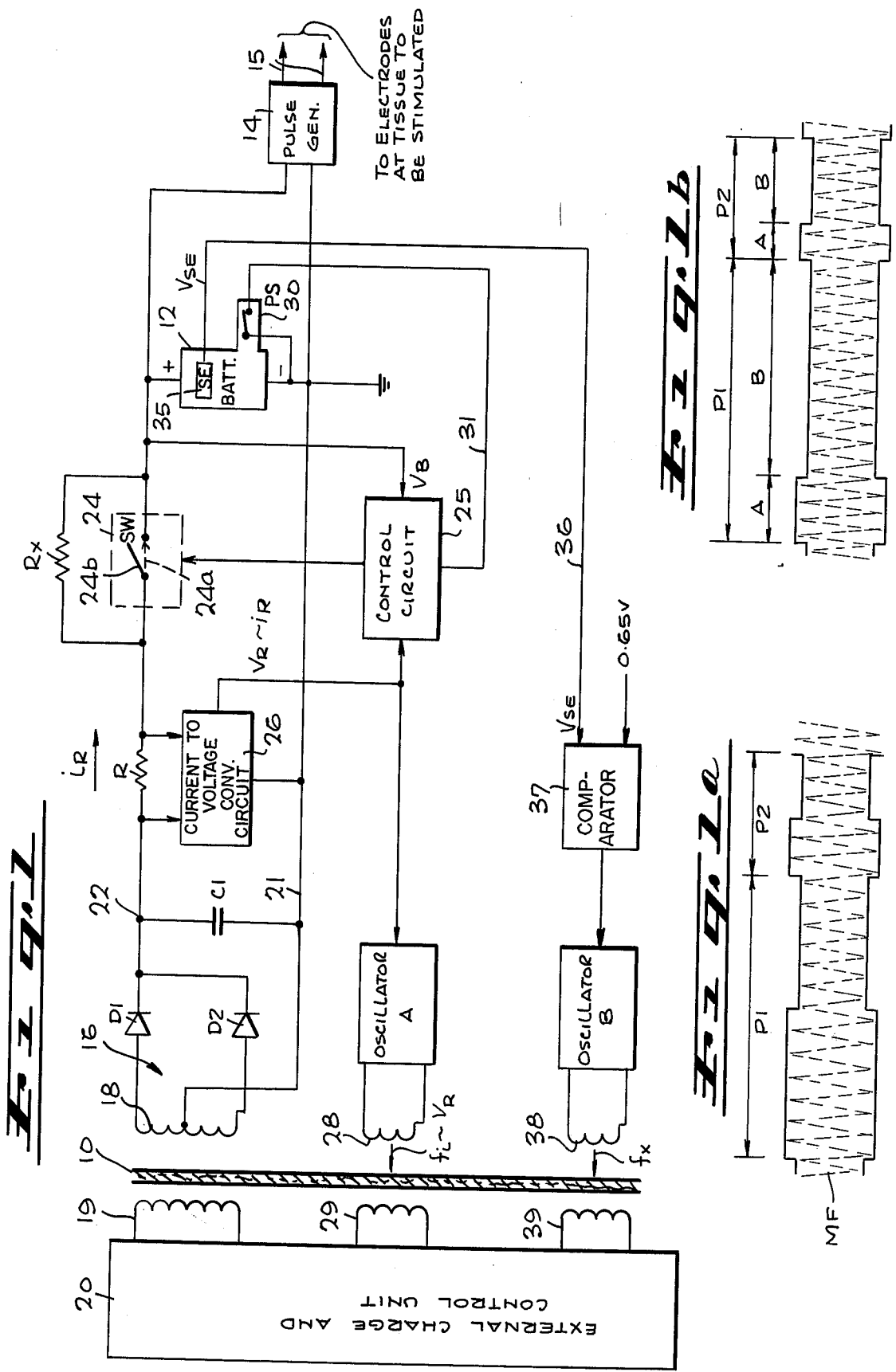

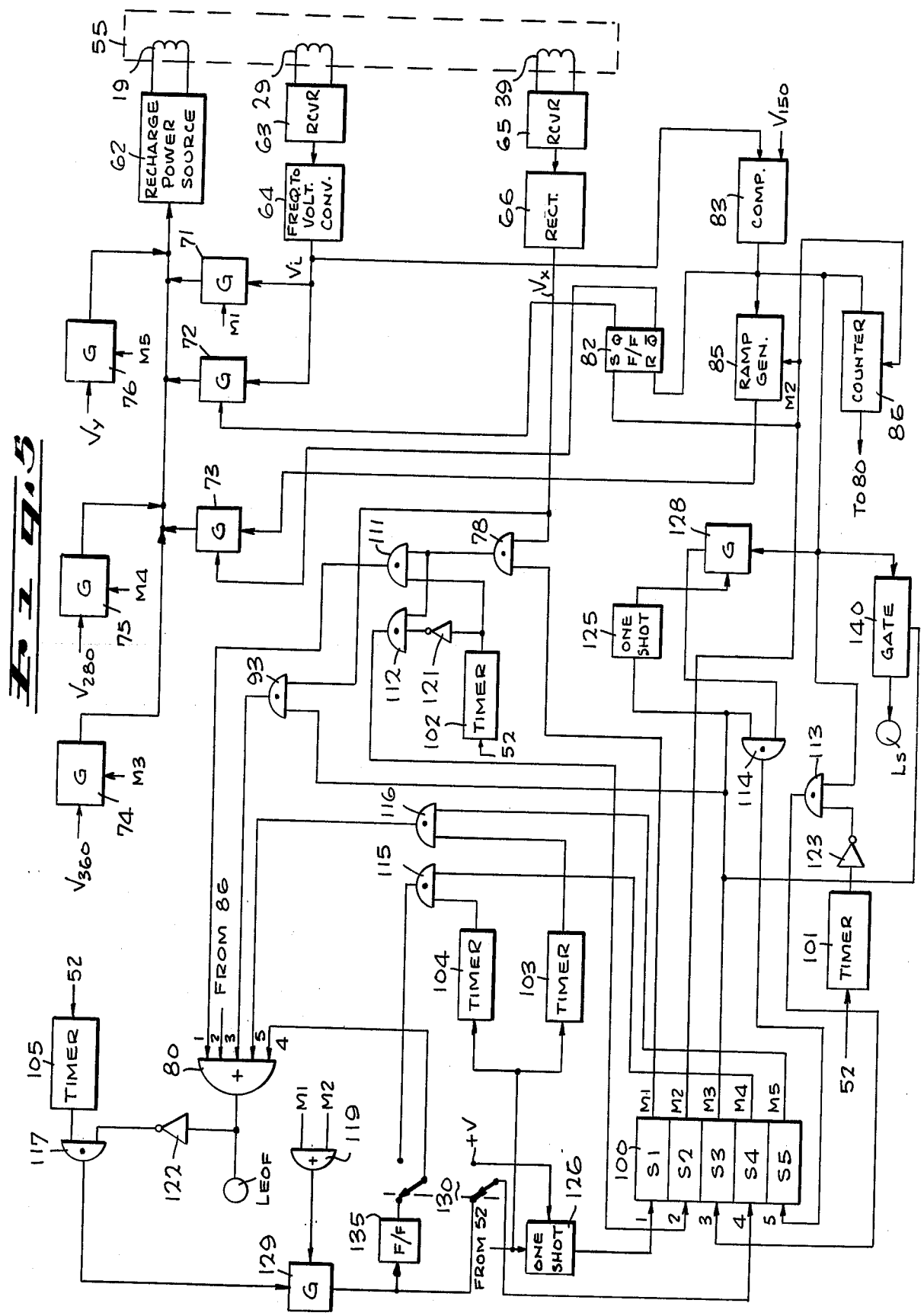

MULTIMODE RECHARGING SYSTEM FOR LIVING TISSUE STIMULATORS

BACKGROUND OF THE INVENTION

1. Field of the Invention

The present invention generally relates to a living tissue stimulator system and, more particularly, to a living tissue stimulation system with a rechargeable power source and charge control means.

2. Description of the Prior Art

In recent years advances have been made and systems proposed for the use of electrical stimulation of living tissue, such as nerves, muscles and the like. U.S. Pat. No. 3,083,712 describes a device for producing electrical muscle therapy. The use of electrical stimulation of living tissue in the treatment of epilepsy, cerebral palsy and spasticity is described in an article entitled "Effect of Chronic Stimulation of Anterior Cerebellum on Neurological Disease", Lancet 1:206, 1973. The stimulation of different living tissues is described in other prior art publications, e.g., a report entitled "Functional Neuromuscular Stimulation", published by the National Academy of Sciences, Washington, D.C. in 1972.

The most widely used and best known device which provides electrical stimulation of living tissue is the cardiac pacer. Briefly, the cardiac pacer is a device designed to provide electrical stimulating pulses to the heart. One type of cardiac pacer, known as the fixed rate cardiac pacer, provides stimulating pulses to the heart, irrespective of proper heart beating, while another type, known as the demand inhibited cardiac pacer, provides a stimulating pulse only when the heart fails to provide a proper natural pulse. The pacer, regardless of type, usually includes a source of power, e.g., a battery which powers a pulse generator. The latter generates the pulses which are applied to the patient's heart by means of one or more electrodes located at the heart and electrically connected to the generator by electrode leads.

The very early implanted cardiac pacers, i.e., those implanted inside the patient's body, included a small battery which required periodic replacement, thus necessitating periodic surgeries. To overcome this disadvantage a cardiac pacer was developed which includes a battery which is rechargeable with energy from a source, external to the body. Such a pacer is described in prior-art references, including U.S. Pat. Nos. 3,867,950, 3,888,260 and 3,942,535.

Briefly, the implanted pacer includes a charging circuit which is energized by external energy, such as an alternating magnetic field. The charging circuit in turn produces a charging current, which is made to flow to the rechargeable battery, thereby recharging the latter. The implanted charging circuit and the rechargeable battery can of course be used in any implanted living tissue stimulator or pacer, used to stimulate tissue, other than the heart. As used herein the term pacer intends to refer to any pacer implanted in a patient's body to provide stimulating pulses to the heart or any other tissue to be stimulated. That is, it is not intended to be limited to a cardiac pacer.

Although the implanted charging circuit with the rechargeable battery eliminate the need for frequent surgeries to replace batteries, their use in the pacer has developed many design problems, only some of which have been solved by the prior art. It was discovered that when recharging the battery it is important to be able to monitor the charging current as well as the battery state of charge, to insure that the battery is being properly charged and that the charging current does not exceed a maximum current level, which may permanently damage the battery. Also, it is important to prevent the battery from being overcharged above a safe level.

In U.S. Pat. No. 3,888,250 an implanted cardiac pacer is described in which the charging current is monitored and a signal, whose frequency is related to the current amplitude, is transmitted external to the patient. In U.S. Pat. No. 3,942,535 similar means are described. More recently, a tissue stimulation system has been proposed in which at least one switch is incorporated in the path of the charging current and special sensors are coupled to the battery to determine its state of charge. The combined function of the switch and the special sensors is to control the battery charging so that it does not exceed a desired charged state.

These battery-protection devices, namely, the switch and the special sensors perform their intended function only when they perform properly. However, if one or more of them fail, a danger exists that they will either not protect the battery from becoming over-charged above a safe level and thereby become permanently damaged, or that they will cause signals to be transmitted external to the patient which may be interpreted as indicating that the battery is properly charged, when in fact it is not. In the prior art system the battery-protection devices, are assumed to be fail-proof, which in fact they are not. The prior art system does not include any means, whether implanted or external, with which the malfunctioning of one or more of these battery-protection devices can be determined, nor means for providing a safe charging current to the battery even when one or more of the battery-protection devices have failed.

The life of a patient with an implanted pacer often depends on the pacer's proper operation, for which a properly charged undamaged battery is an absolute requirement. A presently existing implanted pacer with a rechargeable battery has an expected life of many years, e.g., 10 years or more, if only the battery can be protected properly by the protection devices, to prevent the battery from being overcharged above a safe level and/or preventing the battery from being charged by an excessively high charging current. Thus, a need exists for a stimulation system incorporating, an implanted pacer with a rechargeable battery, in which the battery, though protected by protection devices, can be charged safely even when one or more of these protection devices fail. Alternately stated, a need exists for a living tissue stimulation system, with an implanted pacer with a rechargeable battery and battery-protection devices, the system being operable so as to sense failure of any of the devices and in spite of such failure or failures be able to safely charge and protect the battery from permanent damage.

OBJECTS AND SUMMARY OF THE INVENTION

It is a primary object of the present invention to provide an improved living tissue stimulation system.

Another object of the present invention is to provide a new living tissue stimulation system with an implanted pacer including a rechargeable battery and battery-protection means, and external means capable of determining any malfunctioning of one or more of said battery protection devices.

A further object of the invention is to provide a new improved living tissue stimulation system with which adequate and safe charging of an implanted rechargeable battery can take place in spite of malfunctioning of one or more implanted battery-protection devices.

These and other objects of the invention are acheived by providing an implanted pacer with a rechargeable battery, charging circuitry and battery-protection devices. Also, included are devices which transmit signals external to the body which are indicative of recharging current amplitude and the battery state of charge. External to the patient a recharger and control unit is provided. It receives the transmitted signals and based thereon is operated in any one of several modes so that even if one or more of the implanted battery-protection devices fail, recharging power at a safe level is provided to the implanted battery for a duration sufficient to recharge it to a proper charged state.

With the present invention since the actual state-of-charge of the battery is monitored, the battery can be charged safely at a very high rate, i.e., with a high amplitude charging current until the battery reaches a selected state-of-charge, which is typically close to or equal to its fully charged state. Thus, battery charging time can be reduced significantly, which is most convenient for the patient, and the doctor, if charging takes place in the latter's office. Also, with the present invention, as will be clear from the following description the battery when reaching the desired state of charge may be charged at the battery trickle charge rate. The latter is a rate at which the battery can be charged continuously without damaging it, independent of its state-of-charge.

The novel features of the invention are set forth with particularity in the appended claims. The invention will best be understood from the following description when read in conjunction with the accompanying drawings.

BRIEF DESCRIPTION OF THE DRAWINGS

FIG. 1 is a combination block and schematic diagram of one embodiment of the invention;

FIGS. 1a and 1b are simplified diagrams of modulated waveforms useful in explaining one method of transmission of signals;

FIGS. 4 and 5 are circuit diagrams of two different embodiments of the system's portion, external to the body of a patient.

DESCRIPTION OF THE PREFERRED EMBODIMENTS

Figure 3:
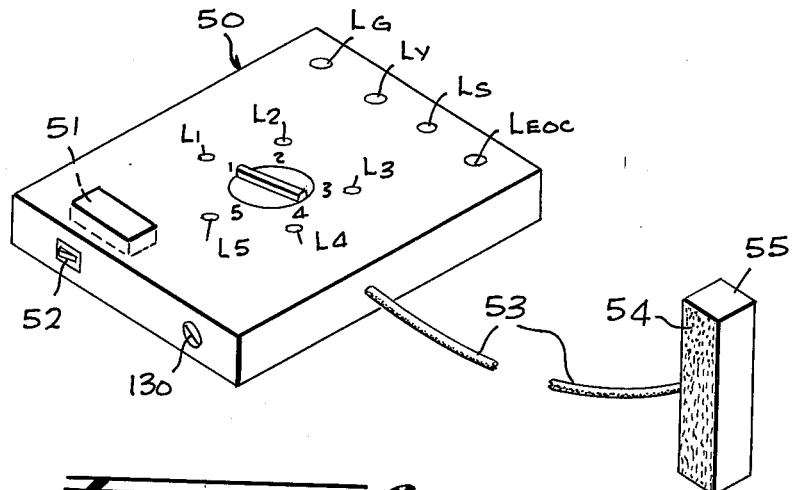
FIG. 3 is an isometric view of one possible embodiment of the external portion of the system of the present invention.
Figure 2:
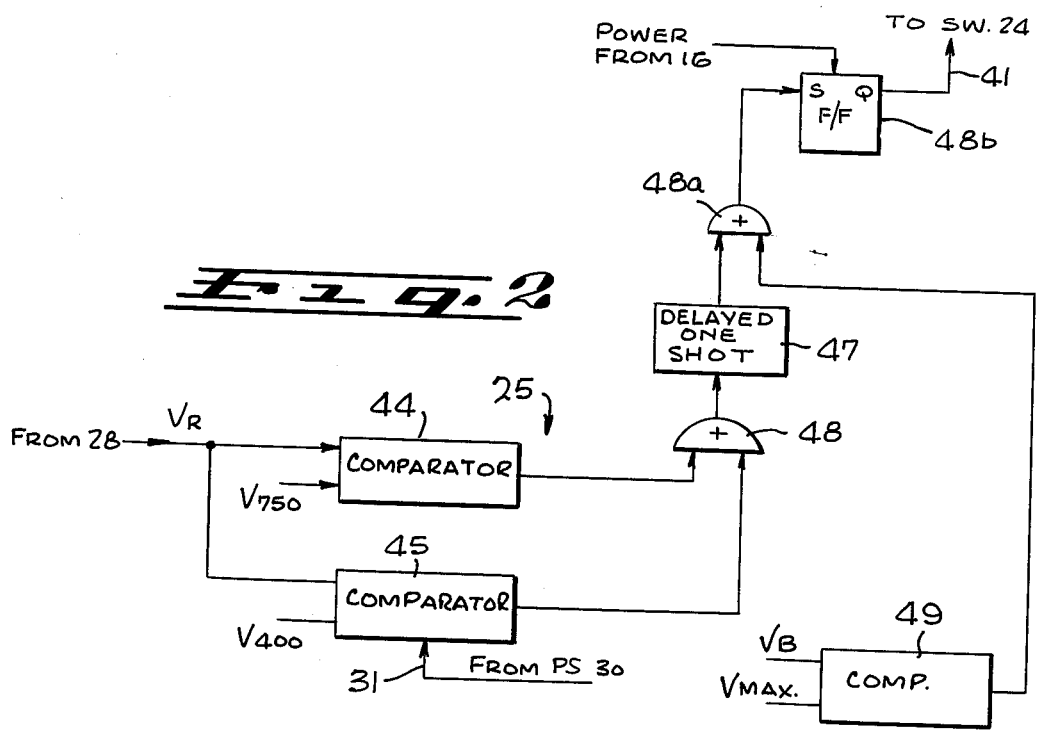
FIG. 2 is a detailed block diagram of one embodiment of the control circuit, shown in FIG. 1.

Attention is first directed to FIGS. 1, 2 and 3 in connection with which the basic principles of the invention will be described. In FIG. 1, numeral 10 represents a patient's skin. The circuitry to the right of skin 10 represents a pacer, implanted in a patient under the skin. Thus, all the pacer's parts are implanted in the body. The circuitry to the left of the skin 10 represents circuitry external to the patient's body. FIG. 2 is one possible embodiment of an implanted control circuit shown in block form in FIG. 1, while FIG. 3 is an isometric view of the external portion of the stimulation system in accordance with the present invention.

In FIG. 1, numeral 12 designates a rechargeable battery, e.g., a nickel-cadmium (Ni—Cd) cell, which is used to supply power to a pulse generator 14. The latter is assumed to generate output pulses which are applied to one or more electrodes (not shown) which are located at the tissue to be stimulated, by means of one or more electrode leads 15. The pulse generator 14 is shown in block form since it does not form part of the invention. It may be similar to any of the pulse generators described in any of the above-mentioned U.S. patents. Also, it may consist of any pulse generator designed to produce stimulation pulses for stimulating selected living tissue, such as muscles, nerves and the like.

The implanted pacer includes a charging circuit 16 which receives charging energy from a source, located external to the patient, and provides a charging current which is applied to the battery 12, in order to recharge the latter. For explanatory purposes, it is assumed that the charging energy is supplied to charging circuit 16 by magnetic induction, although it should be appreciated by those familiar with the art that energy may be transferred through skin 10 to circuit 16 by means other than magnetic induction. For example, energy may be transferred by light waves, visible or infrared, using solar cells or other light to current flow energy transducers as the pickup device. Also, energy transfer may be by means of sound or vibration waves (subaudible, audible or ultrasonic) by using a piezoelectric crystal or other vibration to current energy flow transducers.

Assuming energy transfer by magnetic induction the charging circuit 16 includes a pickup winding or coil 18. In coil 18 an alternating current is induced by an alternating magnetic field, produced external to the body when an alternating current is made to flow through an external winding or coil 19, which forms part of an external charge and control unit 20, hereinafter simply referred to as the external unit 20. The windings 18 and 19 may be viewed as the primary and secondary windings of a transformer, so that when primary winding 19 is externally located proximate to the implanted winding 18 current in winding 19 induces a corresponding current in winding 18.

In FIG. 1, the center tap of winding 18 is shown connected to line 21, which is assumed to be at ground potential or simply ground, while the ends of windings 18 are connected to a junction point 22 through rectifying diodes D1 and D2. Thus, the AC current across winding 18 is rectified to produce a DC voltage at junction 22. A filtering capacitor C1 is shown connected between junction point 22 and ground. If desired, a synchronous switching rectifier may be used for D1 and D2 to obtain higher rectification efficiency.

The DC voltage at 22 is applied to the battery 12 through serially connected resistor R and an On-Off switch 24. When the switch in the On or closed state (as represented by dashed line 24a) it provides a substantially zero resistance path across it for the DC current to the battery 12. However, in the Off state (as shown by line 24b) the switch 24 is open (Off), thus inhibiting the flow of current therethrough. The switch position is under the control of a control circuit 25. In FIG. 1, the switch 24 is shown as a mechanical switch for explanatory purposes only. In practice, it may comprise a solid state switching device, such as a transistor which can be turned to full conduction or cutoff, i.e., On or Off by control circuit 25.

As shown in FIG. 1, a bypass resistor $R_x$ is connected across switch 24. As will be explained hereinafter its function is to provide a path for battery recharging current even when switch 24 is open. The switch resistance of $R_x$ is quite large. Assuming a constant voltage at junction point 22 the charging current amplitude applied to the battery is directly related to the resistance in the path between junction 22 and the battery. For explanatory purposes, ignoring the equivalent source resistance of coil 18, with switch 24 closed only resistor R is in the current path. However, when switch 24 is open the path resistance is that provided by R plus $R_x$. The latter's resistance is quite large so that for any given voltage at 22 the current amplitude through R and $R_x$, when 24 is open, is a small fraction of the current when switch 24 is closed, thus shorting out $R_x$ and only R is in the current path. For explanatory purposes let it be assumed that under normal operating conditions with switch 24 closed, the charging current through R is 600ma, while with switch 24 open, the current drops to 100ma. That is, the current decreases by a factor of six due to the resistor $R_x$.

The voltage across resistor R, which is directly related to the current $i_R$, which flows through R, and which is the current applied to recharge the battery, is applied to a circuit 26. The output of the latter, designated $V_R$, is a voltage with respect to ground, which is directly related to the current $i_R$ through R which is the charging current applied to the battery.

The implanted pacer, shown in FIG. 1, includes means similar to those described in some of the above-mentioned patents, e.g., U.S. Pat. No. 3,942,535. It includes means for transmitting a signal external to the patient to indicate the battery charging current amplitude. In FIG. 1, these means are shown comprising a voltage controlled oscillator A to which $V_R$ is applied. Oscillator A includes an output coil 28 which acts as an antenna, transmitting a signal at a frequency which is related to the amplitude of $V_R$, which is in turn related to the battery charging current amplitude. The transmitted signal frequency is generally designated by $f_i$.

For explanatory purposes it is assumed that the external unit 20 includes a pickup coil 29 which picks up the transmitted signal. In unit 20, a receiver, connected to coil 29, converts the frequency $f_i$ of the received signal into a corresponding voltage $V_i$, indicative of the amplitude of the battery charging current $i_R$. The use of this voltage ($V_i$) will be described later in connection with FIGS. 2, 4 and 5. In practice coils 28 and 29 can be viewed as the primary and secondary coils of a transformer. The current at $f_i$ in the primary coil 28 induces a current at the same frequency in secondary coil 29.

As shown in FIG. 1 the voltage $V_R$ is also applied to the control circuit 25. In addition, two other input signals are applied to circuit 25. One of these is the voltage across the battery 12, designated $V_B$. The other input is from a pressure switch (PS) 30. The pressure switch 30 is connected to the battery 12 and senses its internal pressure. As is known the battery internal pressure is directly related to its state of charge. The function of PS 30 is to provide a signal, via line 31 to control circuit 25 when the battery reaches a preselected charge state. For example, let it be assumed that PS 30 provides a signal on line 31 when the battery reaches a fully charged state, represented by 1C. Although various pressure switches or pressure to voltage transducers may be used, for explanatory purposes PS 30 is shown as a mechanical switch which closes, so as to ground line 31, when the battery is fully charged.

In addition, the pacer is assumed to include an electrode 35 located within the battery 12. This electrode is assumed to provide an output voltage whose amplitude is related to the state of charge of the battery. In practice, an electrode sensing any parameter that changes with the battery state of charge may be used. For example, an electrode sensing oxygen pressure which is related to the battery state of charge may be employed. Such an electrode is sometimes referred to by those familiar with the art as an oxygen or signal electrode. Hereinafter, electrode 35 will be referred to as the signal electrode or SE 35. As shown in FIG. 1, a line 36 which is connected at one end to SE 35 extends out of battery 12. The voltage on line 36, designated $V_{SE}$, is the voltage of SE 35.

For explanatory purposes only let it be assumed that when the battery reaches a charged state of 0.85C, i.e., 85% of full charge, the voltage $V_{SE}$ equals 0.65 volt. In accordance with the present invention it is desired to provide an indication external to the patient, when the battery charged state is slightly below full charge, e.g., 0.85C, i.e., when $V_{SE} = 0.65v$. This may be achieved in different ways.

One simplified arrangement, presented herein for explanatory purposes, is shown in FIG. 1. Therein, a separate oscillator B with its output coil 38 are shown. Briefly, the voltage $V_{SE}$ on line 36 is compared by a comparator 37 with a voltage of 0.65v. When $V_{SE} = 0.65v$ the output of comparator 37 is assumed to go high or positive with respect to ground, thereby activating oscillator B to transmit, via coil 38, a signal at a fixed frequency $f_x$. The frequency $f_x$ is outside the range of frequency $f_i$. Associated with coil 38 is an external pickup coil 39 which forms part of external unit 20. Coil 39 picks up the transmitted signal at $f_x$ from coil 38 and supplies it to a receiver which provides a preselected output voltage, hereinafter referred to as $V_x$, only when the signal at $f_x$ is transmitted by coil 38, i.e., only when $V_{SE} = 0.65v$, indicating that the battery reached 85% of its full charge. The use which is made of voltage $V_x$ in external unit 20 will be described hereinafter.

It should be appreciated that if desired the voltage $V_{SE}$ on line 36 may be supplied directly to oscillator B. Its output frequency $f_x$, instead of being constant, will vary as a function of $V_{SE}$. The frequency $f_x$ induced in coil 39, may then be converted into a voltage in the external unit 20 and compared with a selected reference voltage to produce $V_x$ only when $V_{SE} = 0.65v$, i.e., only when the battery has reached 85% of full charge. That is, the voltage comparison, performed by comparator 37, may be done externally, rather than in the implanted pacer.

From the foregoing it is thus seen that in accordance with the present invention one signal is transmitted external to the body which is related to the charging current amplitude, i.e., to the battery charging rate. A second signal is transmitted to indicate when the battery has reached a selected state-of-charge, i.e., the state-of-charge of the battery. It should be pointed out that herein the state-of-charge of the battery is monitored directly rather than by measuring the voltage across the battery and using the latter to interpret the state-of-charge. The voltage across the battery is not a sufficiently reliable indication of the state-of-charge. For example, when a battery fails in a high impedance state, the voltage across it may be high even though the state-of-charge of the battery may be very low.

It should be stressed that various signal transmission techniques may be employed to transmit the desired signals from the body. For example, when magnetic induction is used to transmit the recharging power by means of an external magnetic field the signals may be transmitted by selectively loading the magnetic field, so as to amplitude modulate it by a small percentage and combine it with pulse width modulation to thereby transmit both the charging current and state-of-charge indicating signals.

The latter techniques may be explained briefly in connection with FIGS. 1a and 1b. Assuming that the magnetic field frequency is relatively high, e.g., 20KHz the current amplitude-indicating signal may be transmitted by loading and unloading the magnetic field as shown in FIG. 1a, at a frequency related to the current amplitude. In FIG. 1a, P1 represents one cycle indicative of one current amplitude, and P2 represents one cycle indicative of another current amplitude. The magnetic field amplitude is unloaded during one half of each cycle and loaded during the other cycle half. The high frequency of the magnetic field is designated by MF. The amplitude modulation frequency is generally much lower, e.g., in the range of a few hundred Hz. Such a signal transmission technique is described in U.S. Pat. No. 3,942,535. The signal electrode voltage may be transmitted by pulse width modulating the ratio of each cycle, during which the field is loaded and unloaded, as shown in FIG. 1b. Therein the unloaded and loaded portions of each cycle are represented by A and B respectively. The unloaded portion A is shown as only 25% of the cycle. It should be apparent that if desired the signal may be indicated with an absolute value of A independent of the modulation frequency or as the ratio of A to B in each cycle.

The switch 24, which is under the control of control circuit 25, the pressure switch 30 and SE 35 can be viewed as implanted battery-protection and charge completion indication devices. These devices, hereinafter simply referred to as the battery protection devices, are used to protect the battery from being damaged by a large charging current, e.g., 600ma lasting a relatively long period, e.g., several minutes when the battery has already been charged up to a high state of charge. Also, these devices function to indicate that the battery is approaching or has reached a fully charged state. Thus, these devices enable a depleted battery to be charged safely at a high rate that would have been unsafe for a fully charged or nearly fully charged battery.

If the battery protection devices were fail-proof it would have been possible to protect the battery with fewer protection devices and components. For example, if the SE 35 were fail-proof the pressure sensor 30 would not be required. One could rely on SE 35 to provide an indication when the battery reaches 85% of full charge, and would not need the pressure switch 30 which is designed to provide an indication of a battery charged state which is higher than 85%, e.g., 100% (1C). Similarly, if switch 24 were fail-proof the bypass resistor $R_x$ would not have been required.

However, for long implanted periods, e.g., in excess of 10 years, it is not known of switch 24, pressure switch 30 and SE 35 are totally fail-proof. It is quite possible that one of these devices might fail in either an open or closed state. For example, pressure switch 30 may fail in a closed state thereby grounding line 31 even before the battery is fully charged, or in an open state in which line 31 is never grounded, regardless of the battery charged state. Similarly, SE 35 may fail in a closed state, so that $V_{SE} > 0.65v$, even before the battery is recharged to 85% of full charge, or in an open state in which $V_{SE} < 0.65v$ is present on line 36 even though the battery is charged to above 85%. Likewise the switch 24 may fail in either state. For example, it may fail in an open state in which it remains open regardless of the control signal supplied thereto by circuit 25 via line 41.

The novel system of the present invention is designed to effectively monitor not only the charging current applied to the battery and its state of charge, but also the operations of the portection devices, switch 24, pressure switch 30 and SE 35. This is achieved by interpreting the signals transmitted to the external unit 20 from the start of a battery charging operation, to determine, which, if any, of the protection devices has failed and if it failed in what state. Based on such determination, the charging current amplitude is controlled by controlling the power provided by the external unit 20 to protect the battery even though one or more of the protection devices have failed.

As will be pointed out hereinafter in great detail the external unit 20 is operable in any one of several modes. The operating mode is chosen after determining which if any of the protection devices failed and the failure state. The operating mode may be selected manually or automatically, as will be described hereinafter. One can view the invention as a communication system in which the implanted pacer is inaccessible and from which signals are received. These signals are interpreted to determine failure of any devices in the pacer and based on the detected failure the signal which is sent back to the pacer is controlled. In the present invention the externally generated power, in the form of the alternating magnetic field, is controlled by controlling the field intensity or magnitude.

Figure 4:
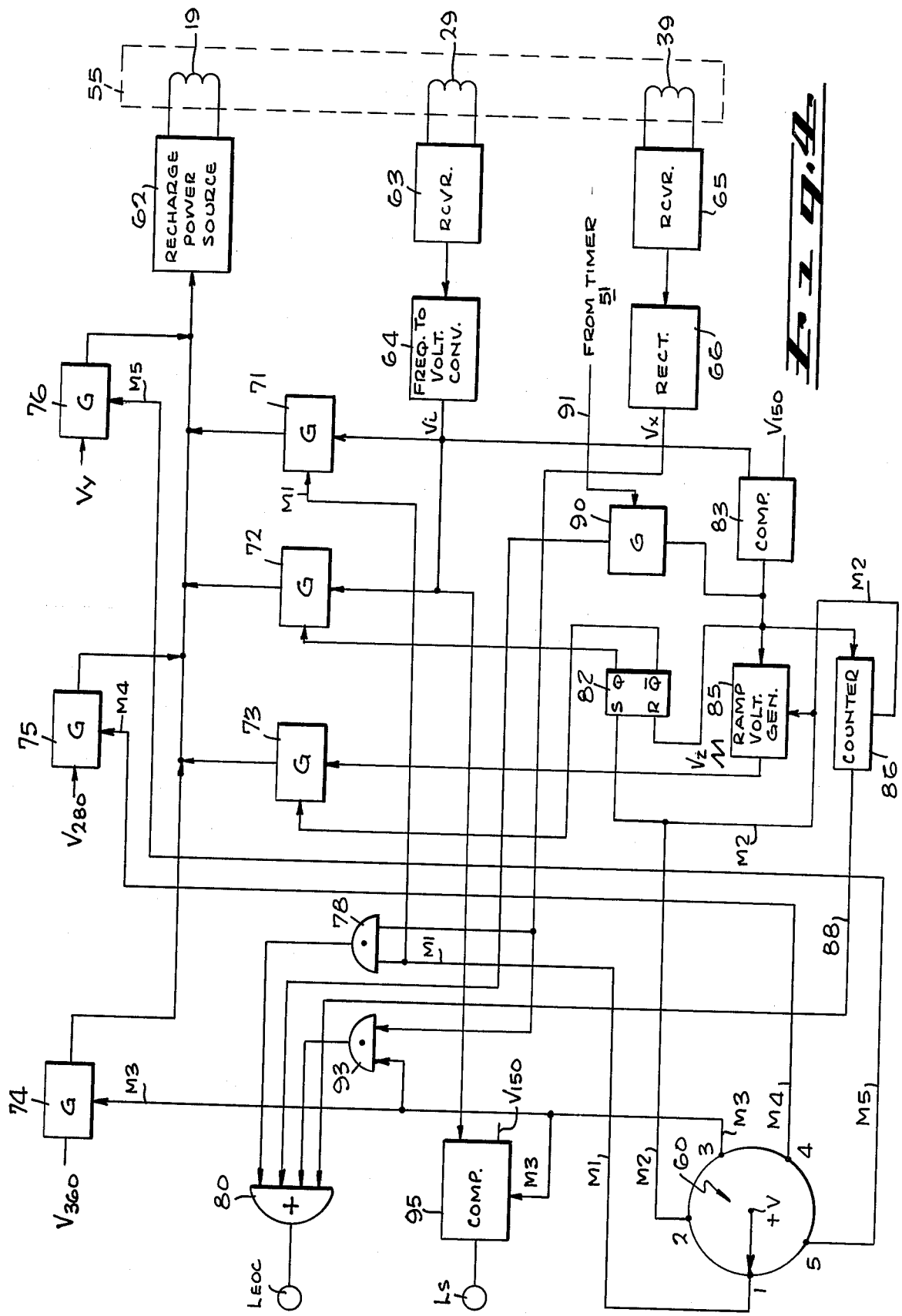

Before describing the external unit 20 in connection with FIGS. 3, 4 and 5, attention is directed to FIG. 2 which is one possible embodiment of control circuit 25. The function of the circuit 25 is to open switch 24 when any one of the following three conditions exists:

1. When the charging current $i_R$, as represented by $V_R$, reaches an excessively high amplitude, e.g., 750ma and lasts for a selected duration, e.g., 10 seconds.

2. When pressure switch 30 grounds line 31, e.g., when the battery reaches a fully charged state (1C) and the charging current is greater than the maximum trickle charge rate of the battery, assumed to be not greater than 400ma.

3. When the battery 12 is failing in a high impedance mode and therefore the voltage $V_B$ thereacross equals or exceeds a selected safe voltage, designated $V_{MAX}$.

As shown in FIG. 2 control circuit 25 includes two comparators 44 and 45, each having one input to which $V_R$ from circuit 28 is applied. As previously pointed out the amplitude of the voltage $V_R$ depends on the charging current ($i_R$) amplitude. In comparator 44, $V_R$ is compared with a reference voltage $V_{750}$. The voltage $V_{750}$ has an amplitude which equals that of $V_R$ when the charging current is 750ma. When the charging current is 750ma or above, representing a dangerously high current, $V_R \geq V_{750}$. Consequently, the output of comparator 44 is assumed to go high. It activates an Or gate 48, which in turn activates a delayed one shot 47 with a selected delay, e.g., 10 seconds. If the charging current $i_R \geq 750$ma lasts for 10 seconds or more the outputs of comparator 44 and Or gate 48 stay high for 10 seconds or more. At the end of the 10 second period the output of one shot 47 goes high, activating an Or gate 48a, which in turn activates or sets an electronic latch 48b which latches the switch 24 in its open state.

The latch 48b is assumed to be powered by the charging circuit 16, during a recharging operation. In FIG. 2 it is shown as a flip flop (FF) which is set by the high output of Or gate 48a. Once set it is assumed to remain set (and switch 24 remains open) irrespective of $i_R$, until the charging field is very low, which for all practical purposes is assumed to be turned off. For explanatory purposes the latch 48b will be assumed to be reset when the charging field from external unit 20 is turned off so that the charging current amplitude $i_R$ is of substantially zero amplitude. If however, $i_R$, after first equalling or exceeding 750ma drops below 750ma before the lapse of 10 seconds the outputs of comparator 44 and Or gate 48 fail low before the 10 seconds. Consequently, the output of the delayed one shot 47 does not go high, and therefore Or gate 48a does not set latch 48b. As a result, the switch 24 is not opened, and it remains closed.

The excessive (750ma) current amplitude may occur if: (a) the external unit 20 does not regulate the charging field, based on the current-indicating signal which is transmitted thereto as a feedback signal, or (b) oscillator A has malfunctioned.

The comparator 45, to which $V_R$ is supplied, is operative only when line 31 is grounded, i.e., when the pressure switch 30 is closed, which occurs when the battery is charged to a 1C state (fully charged), as hereinbefore assumed for explanatory purposes. Comparator 45 is also supplied with a reference voltage $V_{400}$. $V_R \geq V_{400}$ when $i_R \geq$ 400ma. Thus, when line 31 is grounded and $i_R \geq$ 400ma, the output of comparator 45 goes high, enabling gate 48. If $i_R \geq$ 400ma for more than 10 seconds, one shot 47 activates Or gate 48a to drive FF 48b to its set state to open switch 24. Again, once FF 48b is set, it is reset only if the charging field is turned off, i.e., $i_R$ drops to zero. However, when FF 48b is reset, as long as $i_R <$ 400ma even though line 31 may be grounded, the output of comparator 45 is low and therefore it does not enable gate 48 and the following circuits and switch 24 remains closed.

Circuit 25 also includes a third comparator 49 to which $V_B$, i.e., the voltage across the battery and a reference voltage $V_{MAX}$ are supplied. Whenever, due to an open failure, namely a high impedance failure of battery 12, $V_B \geq V_{MAX}$ the output of comparator 49 goes high, thus enabling gate 48a to open switch 24 by setting FF 48b. As seen, the over voltage protection does not have the time delay, e.g., 10 seconds, since when the battery fails in the high impedance mode it is desirable to open switch 24 quite rapidly so as to reduce high charging currents to prevent any damage to the battery. As will be pointed out hereinafter the opening of switch 24 due to battery high impedance failure may be distinguishable from other switch openings, to enable an operator to distinguish between battery failure and switch openings caused for other reasons. It should be pointed out that except for the pulse generator 14, which is powered by battery 12, all the other implanted circuits in the pacer may be powered by power from the charging circuit during a charging operation, to reduce the drainage of the battery.

Attention is now directed to FIG. 3 which is an isometric view of one possible embodiment of the external unit 20. It includes a console unit, or simply console 50, wherein all the circuitry of external unit 20, except for coils 19, 29 and 39, are assumed to be housed. The console 50 further includes display devices such as light indicators, a visually displayable timer or clock 51 and switches, including an On-Off switch 52 which is used to turn unit 20 On or Off. As previously explained coil 19 is the power (alternating magnetic field) transmitting coil and coil 29 is the pickup coil of the signals transmitted from the implanted power of a frequency $f_i$, where $f_i$ is related to the charging current $i_R$. The third coil 39 is one in which a signal is induced at the fixed frequency $f_x$ when the signal electrode 35 provides a selected voltage (0.65v), indicating that the battery reached a selected charged state (e.g., 85% of full charge = 0.85C).

These three coils are housed in a separate small charging head 55, and are connected to the circuitry in console 50 by a cable 53. The head 55 may be provided with a contact surface 54, designed to attach itself to a contact surface of a vest or the like (not shown) worn by a patient, so as to facilitate the proper positioning of the head with its coil with respect to the implanted coils. Such an arrangement is described in U.S. Pat. No. 3,942,535 in connection with FIGS. 6 and 8.

Briefly, in the circuitry in console 50, the signals from coil 29 at $f_{i \approx iR}$ are converted by a frequency to voltage converter to produce a DC voltage, hereinafter designated $V_i$, whose amplitude is related to the charging current amplitude $i_R$. In normal operation $V_i$ is used as a feedback signal to the charge power source in the console to control the power provided by the power source, so that when the charge head 55 is properly aligned against the skin with respect to the implanted pacer the charging current is at a desired amplitude, herein assumed to be 600ma. When the head 55 is properly aligned and 600ma of charging current flow to the battery a light $L_G$, assumed to be a green light, is illuminated. However, during head alignment or whenever the current is less than 600ma another light $L_Y$, assumed to be a yellow light, may be illuminated. The latter may be illuminated continuously or caused to flash On and Off as long as the charging current is less than 600ma. Such an arrangement is also described in U.S. Pat. No. 3,942,535, with $L_G$ and $L_Y$ corresponding to the light-emitting diodes (LEDs) 26 and 27, shown in FIG. 5 therein.

Unlike the prior art the external unit 20 includes in console 50 circuitry which enables proper charging of the battery even though one or more of the battery-protection devices such as switch 24, PS 30 and SE 35, hereinbefore described, fail. In accordance with the present invention the recharge power source is controlled not only by the feedback voltage $V_i$, which is generated with an amplitude proportional to the charging current $i_R$, as is the case in the prior art. The external unit 20 is operable in any of several modes. Hereinafter, the invention will be described in connection with an embodiment with fives modes of operation, referred to as mode 1 (M1) — mode 5 (M5). Only in some of these modes is $V_i$ fed to the power source. The selected mode depends on which of the battery protection devices failed and the type of failure, which is detected.

Initially the invention will be described in which an operator manually selects the mode of operation. Thereafter an embodiment capable of automatic mode selection will be described. For manual mode selection the console 50 is assumed to include a five-position mode switch 60 with the positions being indicated by numerals 1-5. In FIG. 3 the switch is shown in the mode 1 position, which is the first mode, generally chosen after turning the system On by means of On-Off switch 52. To aid in describing the invention let it be assumed for explanatory purposes only that the battery has a charging capacity of 1000mah (milliamp hour) and that based on the time elapsed since the last charging operation the battery is assumed to be nearly fully discharged, e.g., at a charged state of 0.13C (13%). Based on the above assumptions it would require a charging period of 1.2 hours or 72 minutes at 600ma for the battery to reach the state of charge of 85% in which SE 35 provides the voltage $V_{SE} = 0.65v$ which causes the transmission of the signal via coil 38 at $f_x$ and which in turn produces a voltage $V_x$ in the console circuitry. To reach full charge so that PS 30 is activated and line 31 is grounded, would require about 1.45 hours or 105 minutes. In the following description of the various modes it will first be assumed that the battery has not failed and that therefore switch 24 is not opened due to battery failure.

MODES OF OPERATION

Mode 1

In this mode all the protection devices are assumed to function properly so that 600ma of charging current is applied to the battery when the head 55 is properly aligned and green light $L_G$ is illuminated or On. Charging continues at 600ma until $V_x$ is produced, which occurs when $V_{SE} = 0.65v$ i.e., the battery reaches a charged state of 85%. When $V_x$ is produced, a light, assumed to be blue and designated $L_{EOC}$ is illuminated (turned On). It is intended to indicate that the desired charged state of the battery has been achieved and that the charging operation should be terminated. Alternately stated, when $L_{EOC}$ is illuminated, it represents an End-of-Charge (EOC) command or indication, thus the subscript "EOC". In mode 1 when $L_{EOC}$ goes On, if it happens after about 72 minutes, as indicated by timer 51, the operator can safely assume that SE 35 functions properly and therefore the End-of-Charge command ($L_{EOC}$) is valid. Thus, the operator turns the system Off (by moving switch 52 to the Off position).

If, however, SE 35 fails by being shorted to the battery positive terminal, hereinafter referred to as the high shorted state, it causes $V_x$ to be produced, irrespective of the battery state of charge. Assuming such a failure occurred, $V_x$ is produced as soon as the system is turned On or at least considerably before the lapse of a 72 minute period. Consequently, when $L_{EOC}$ is On in mode 1, before the expected elapsed time for adequate charging, the operator knows that SE 35 must have failed in the high shorted state, and therefore the End-of-Charge command ($L_{EOC}$ On) is invalid and should be ignored. Under such conditions the operator switches mode switch 60 to position 2, i.e., switches the system to operate in mode 2.

Mode 2

This mode can be thought of as either a backup mode for mode 1 as a primary mode. In it, the high shorted condition of SE 35, i.e., the produced voltage $V_x$ is ignored. Also, it is a mode in which both the switch 24 (see FIG. 1) and the pressure switch (PS) 30 are assumed to operate properly. As previously explained PS 30 is assumed to ground line 31 when the battery charged state is higher than that sensed by SE 35, e.g., a fully charged state. Also, when line 31 is grounded switch 24 opens when the charging current is not less than 400ma. In mode 2, $V_i$ is initially used as the feedback signal and 600ma of charging current are applied to the battery. Then, when the battery reaches the charged state in which PS 30 is activated to ground line 31, assumed to be a fully charged state, since the charging current is 600ma, when line 31 is grounded control circuit 25 opens switch 24, as hereinbefore described in connection with FIG. 2. Once switch 24 opens the current amplitude drops significantly since the current can only flow through the large bypass resistor $R_x$.

For explanatory purposes let it be assumed that the current amplitude drops to a low value, for example 100ma. This drop in current amplitude is sensed by the sudden change in the amplitude of $V_i$. As a result, $V_i$ is no longer used as the feedback signal to the power source. Rather, a voltage $V_z$ from a ramp voltage generator is applied as the feedback signal to the charge power source. $V_z$ is assumed to ramp up from a low voltage level in which the charging current, induced by the charging power source, is 0ma and as $V_z$ increases in amplitude the charging current increases. When $V_z$ is first applied as the feedback signal $i_R = 0$ma. Therefore, latch 48b resets and the switch 24 closes. As $V_z$ ramps up the charging current amplitude increases. When $V_z$ ramps up to an amplitude so that the charging current amplitude is again 400ma, since line 31 is grounded, comparator 45 and the following circuitry in circuit 25 cause the switch 24 to open once more. As a result, the ramp voltage generator is reset, i.e., $V_z$ drops again to an amplitude to produce a charging current of 0ma which causes latch 48b to reset and close switch 24 and starts ramping up once more, until the current is again 400ma which causes switch 24 to open.

In this mode by sensing several successive openings and closing of switch 24 it indicates that the switch 24 and PS 30 operate properly. Consequently, $L_{EOC}$ is turned On to thereby provide a valid End-of-Charge command. If, however, in mode 2 the End-of-Charge command occurs too soon (by looking at timer 51) e.g., before the passage of the expected charging period of 105 minutes, the operator can safely assume that the command is invalid, and is probably due to the failure of PS 30 in a shorted state. That is, PS 30 grounds lines 31, even before the battery reaches full charge and prevents a current equal to or greater than 400ma from reaching the battery by opening the switch 24 whenever the current reaches 400ma. Under such conditions, if mode 2 was used as a primary mode, the operator chooses mode 3. If mode 2 was used as a backup for mode 1, then the operator chooses mode 4 as will be described hereinafter.

Mode 3

This is another backup mode when PS 30 was found to have failed in a shorted state and in which the proper operation of the signal electrode (SE) 35 is relied upon. Since PS 30 is assumed to be shorted, thus preventing the flow of current $i_R \geqq 400$ma, in mode 3, rather than using $V_i$ as a feedback signal, a feedback voltage is applied to the power source to control the latter so that the current $i_R$ is always less than 400ma, e.g., 360ma. The feedback voltage applied to the power source in mode 3 will be designated hereinafter by $V_{360}$. Since the current $i_R$ is held to below 400ma, even though PS 30 is shorted the switch 24 remains closed, and therefore the current of 360ma flows to the battery. Then when SE 35 is activated, i.e., when the battery reaches the selected charged state, assumed to be 85% of full charge, the voltage $V_x$ activates $L_{EOC}$ to provide the End-of-Charge command, just like in mode 1.

Mode 4

This mode is chosen if during a preceding charging operation the End-of-Charge command ($L_{EOC}$ turned On) did not occur after the lapse of a sufficiently long charging period, e.g., 120 minutes. This may occur if both PS 30 and SE 35 fail so that neither of them provides the appropriate signal when the battery reaches the charged state in which the device is designed to produce the appropriate signal. Such failures may be thought of as open-state failures. The absence of the End-of-Charge command after 120 minutes (for the above assumed conditions) indicates to the operator that both PS 30 and SE 35 failed. Thus, the operator turns off the system by means of switch 52. Then when at a later date the battery has to be recharged once more, the operator selects mode 4 by the setting of switch 60. In this mode $V_i$ is not fed back to the power source. Rather, a lower voltage is applied to the power source so that the charging current is relatively low, e.g, 280ma, which corresponds to the battery trickling charge. The feedback voltage applied to the power source in mode 4 will hereinafter be referred to as $V_{280}$. The only disadvantage of this mode is that since the current is relatively low (280ma), as compared with the normal charging current of 600ma, a longer period is required to charge the battery at the lower current. In mode 4 the operator controls the charging period. No automatic End-of-Charge command is produced. It should be pointed out that since in this mode the recharging current amplitude is limited to the battery trickling charge this mode can be used regardless of the indications provided by SE 35 and PS 30 since charging the battery with a current amplitude corresponding to the battery trickling charge will not affect the battery's useful life.

Mode 5

This mode is a backup mode to account for the failure of switch 24 in the open state. When such a failure occurs the current can only flow through the large bypass resistor $R_x$, which greatly limits the current amplitude, as compared with 600ma when switch 24 is closed (thereby shorting out $R_x$). The failure of switch 24 in the open state may be detected when the system operates in mode 3. As previously explained in mode 3 when the current $i_R$ is 360ma, i.e., below 400ma, switch 24 should be in a closed state. In this mode even if the pressure switch PS 30 failed in the closed state, since the current is below 400ma, a shorted pressure switch 30 will not cause switch 24 to open. Thus, if when operating in mode 3 it is sensed (by $V_i$) that the current is considerably below 360ma it indicates that switch 24 has failed in the open state, and a light $L_S$ may be turned On. When light $L_S$ goes On the operator switches to mode 5.

In this mode rather than feeding voltage $V_i$ (which is related to current amplitude) to the power source, a voltage, hereinafter designated as $V_Y$, is fed to the power source. The amplitude of $V_Y$ is chosen to optimize the power supplied to the pacer and thereby optimize the current which can flow to the battery through the large bypass resistor $R_x$, since switch 24 is open. However, as is appreciated the optimum power has to be chosen in order not to cause excessive heating of the implanted parts. For explanatory purposes, it is assumed that in mode 5 $V_Y$ is chosen to cause a current of 100ma to flow through R and $R_x$ to the battery.

As previously explained in connection with FIGS. 1 and 2 whenever the battery fails in an open high impedance state, so that $V_B \geqq V_{MAX}$, switch 24 opens. It may be desirable to be able to distingiush between the failure of switch 24 in the open state and battery failure in the high impedance state. One technique for distinguishing between these two types of failures will be described hereinafter. It should however, be apparent to those familiar with the art that if desired the output of comparator 49 (FIG. 2) need not be used to open switch 24, when the battery fails in the high impedance state so that $V_B \geqq V_{MAX}$. Rather, comparator 49 can be used to activate a separate oscillator (similar to oscillator B) to transmit a signal at a selected frequency (other than in the range of $f_i$ or $f_x$) to the external unit 20 to thereby indicate battery failure. Such a signal may be indicated to the operator or used to automatically stop the charging operation, i.e., turn off the system.

It should be appreciated by those familiar with circuit designs that, based on the foregoing description, many different circuit arrangements may be employed to enable the external unit 20 to operate as described. Different circuits may be arranged to monitor both the battery charged state and the charging current applied thereto, and to control the charging current by controlling the mode of operation of the system, in order to enable the battery to be charged with current, although not necessarily of optimal amplitude, in spite of the failure of one or more of the battery protection devices. Thus, the following description in connection with FIGS. 4 and 5 should be regarded as examples of possible embodiments of external unit 20, rather than to limit the invention thereto.

Attention is now directed to FIG. 4 which is a diagram of an embodiment of the circuitry of external unit 20, in which mode selection is assumed to be performed by an operator, i.e., manually. Therein, numeral 62 designates the rechange power source which applies the power to transmitting coil 19 as hereinbefore described. One example of a possible implementation of power source 62 is described in U.S. Pat. No. 3,942,535. Also, shown in FIG. 4 is a receiver 63 which is connected to coil 29, which acts as receiving antenna for the signals at frequencies $f_i$, transmitted from the pacer by coil 28. The output of receiver 63 is connected to a frequency to DC voltage converter 64 whose output is the voltage $V_i$. The amplitude of $V_i$ is directly related to the charging current $i_R$ flowing through resistor R to the battery. A receiver 65 is connected to receiving coil 39, which receives a signal at frequency $f_x$ only when the signal electrode (SE) 35 output voltage $V_{SE}$ indicates that the battery has reached a desired changed state, hereinbefore assumed to be 85% of full charge. The output of receiver 65 is rectified by rectifier 66 whose output is the voltage $V_x$ of fixed (high) amplitude. $V_x$ is only present when SE 35 senses the desired charged state. Otherwise, $V_x$ is assumed to be of zero amplitude.

In FIG. 4 the mode switch 60 is shown as a simple mechanical rotary switch with five output lines M1–M5. One of lines M1–M5 is high (at +V), depending on the operator-selected mode of operation. Line M1 is high in mode 1, line M2 in mode 2, etc. The circuitry also includes six gates (G) 71–76. These gates control the source of feedback voltage which is applied to the power source 62 to control the transmitted power and thereby control the charging current amplitude in the pacer. As defined herein, any of the gates, designated by G is assumed to provide a path thereacross when it is opened, by a high control signal applied thereto. On the other hand, in the absence of a high control signal the gate is assumed to be closed. When a gate is open the signal or voltage at its input is applied to its output.

In mode 1, gate 71 is open (M1 is high), so that $V_i$ is applied to power source 62. Line M1 is also supplied as one input to And gate 78. The output of rectifier 66, i.e., $V_x$, is also applied to gate 78. When $V_x$ goes high, And gate 78 is enabled and provides a high output to Or gate 80 which is enabled (output high) and activates the End-of-Charge light $L_{EOC}$. If, however, this indication or command happens too soon, e.g., before 72 minutes the operator determines that SE 35 must have failed in a high shorted state. Therefore, the operator advances mode switch 60 to mode 2 in which M2 goes high.

For mode 2 the circuitry includes a control flip flop (FF) 82, a comparator 83, a ramp voltage generator 85 and a counter 86. In mode 2, FF 82 is first set so that its Q output goes high, opening gate 72, in order to apply $V_i$ as feedback to power source 62. Line M2 is also used to enable the generator 85 and counter 86 to operate only in mode 2. Comparator 83 compares $V_i$ with a reference voltage $V_{150}$. The amplitude of the latter corresponds to the amplitude of $V_i$ when the charging current is 150ma.

In mode 2 as soon as PS 30 grounds line 31, which under normal conditions occur when PS 30 senses a pressure corresponding to a desired battery charged state, assumed before as full charge, switch 24 is opened by control circuit 25. Thus, the charging circuit amplitude drops to about 100ma. Consequently, $V_{150} > V_i$ and therefore the output of the comparator 83 undergoes a low-to-high transition. The first such transition indicates the first opening of switch 24. This transition (low-to-high) performs the following three functions when the PS 30 operates properly.

1. It resets FF 82 so that its Q output goes low and $\overline{Q}$ goes high. Thus, gate 72 is closed and 73 is opened.

2. It also resets the generator 85 which provides the voltage $V_z$, which is fed via now open gate 73 to power source 62. When generator 85 is reset, $V_z$ is assumed to drop to a level to result in a charging current of 0ma. Consequently, latch 48b resets and therefore switch 24 closes. Thereafter, $V_z$ ramps up and the current amplitude increases.

3. The counter 86 is clocked to a count of one.

As $V_z$ ramps up the charging current increases, when $i_R \geq 150$ma, $V_i \geq V_{150}$ and therefore the output of comparator 83 goes low. When $V_z$ ramps up so that the current $i_R$ reaches 400ma switch 24 opens up once more, causing $V_i$ to be less than $V_{150}$ and therefore the output of comparator 83 undergoes a second low-to-high transition. This transition, like the first, resets ramp voltage generator 85, to cause $i_R$ to first drop to 0ma and thereafter increase as $V_z$ ramps up, and increments the count in counter 86 by one. After several low-to-high transitions in the output of comparator 83, all counted by counter 86, when the latter reaches a selected count, e.g., 3, its output on line 88 goes high. It enables Or gate 80 to provide the End-of-Charge command or indication by turning on light $L_{EOC}$. It should be pointed out that since in the control circuit 25 a delay is introduced in opening switch 24, the time constant of the ramp voltage $V_z$ should be low enough to account for this delay. Also, instead of a ramp voltage one can use a staircase voltage with sufficient step resolution.

As shown in FIG. 4, the output of comparator 83 is also connected as one input to Or gate 80 through a gate 90. The latter is assumed to be connected to timer 51 by line 91. During the short initial period of mode selection, e.g., the first 2 or 3 minutes, the timer is assumed to cause line 91 to be high, thus keeping gate 90 open. If PS 30 failed in the closed state the switch 24 opens, causing the current to drop and in turn causing the output of comparator 83 to become high. Since gate 90 is open, Or gate 80 is enabled causing $L_{EOC}$ to provide the End-of-Charge indiction. However, since this takes place turning the first few minutes of operation, while the expected charging time is much longer, the operator knows that PS 30 failed in the shorted state. Consequently, mode 2 cannot be used and mode 3 may be selected.

In this mode gate 74 is turned On by M3 being high. Consequently, a reference voltage $V_{360}$ is applied as feedback to power source 62 to control the transmitted power and in turn the charging current to be below 400ma, e.g., 360ma. This current amplitude is below the amplitude which causes the switch 24 to open due to a shorted PS 30. That is, 360ma is below the switch opening threshold of 400ma due to PS 30. Thus, the switch 24 remains closed in mode 3 and the battery is charged with 360ma. Line M3 is also connected to And gate 93. In mode 3 when $V_x$ goes high (SE 35 operates properly and the charged state of 85% is reached) gate 93 is enabled, activating Or gate 80 to turn on $L_{EOC}$.

If, however, when operating in any of modes 1-3 $L_{EOC}$ does not go On after the lapse of a sufficiently long period, e.g., 120 minutes for the above assumed initial conditions, the operator determines that both PS 30 and SE 35 must have failed. The operator therefore terminates the charging operation. Then, during a subsequent charging operation of the same pacer, the operator immediately selects mode 4. In this mode gate 75 is opened by M4 being high, to apply a feedback voltage $V_{280}$. The amplitude of $V_{280}$ is selected so that the charging current as a function of transmitted power is about 280ma, representing the battery trickling current. The length of charging in mode 4 is determined by the operator, based on the time elapsed from the previous charging operation.

The circuitry shown in FIG. 4 includes one additional comparator 95, which is operative only in mode 3. It compares $V_i$ with $V_{150}$. In this mode the current with switch 24 assumed to be closed, is only 360ma since gate 74 is open, by M3 being high, and therefore the feedback voltage to source 62 is $V_{360}$. Thus, PS 30 has no effect on opening switch 24. If switch 24 has failed in the open state, $R_x$ is in series with R. Thus, even though the power from source 62 is one to induce a current of 360ma with switch 24 closed, the current is much less than 360ma. It is less than 100ma. Therefore, $V_i$ drops below $V_{150}$. Consequently, the output of comparator 95 goes high and light $L_S$ is turned On. When $L_S$ goes On it indicates that the switch failed in the open state. Therefore mode 5 is chosen.

In mode 5 gate 76 is opened to apply $V_Y$ as the feedback voltage to power source 62. As previously indicated $V_Y$ is chosen to optimize the transmitted power so as to optimize the charging current through both R and $R_x$ (since switch 24 is permanently open) without adversely affecting the patient. From the foregoing it should thus be apparent that the circuitry shown in FIG. 4 performs all the functions necessary to control the battery charging. Also, based on the circuitry performance the operator can determine which protection devices may have failed and the type of failures, so as to enable the proper selection of the charging mode of operation in spite of failure of one or more of the protection devices.

As previously pointed out the operator selects mode 2 over mode 1, or mode 3 over mode 2 when $L_{EOC}$ is turned on too soon as compared with the approximated required charging time. Also, mode 4 is selected over the other three modes (1–3) if $L_{EOC}$ does not go On after an expected charging duration. On other hand mode 5 is chosen when light $L_S$ goes On, at or soon after the start of the charging operation. It is thus seen that mode selection is based on the presence or absence of indication signals with respect to time references. It should thus be apparent that mode selection may be automated once the system is turned On.

One possible embodiment with automatic mode selection is diagrammed in FIG. 5, wherein elements like those shown in FIG. 4 are designated by like numerals, and perform identical functions to those described before. In FIG. 5, numeral 100 designates a mode selector. It is assumed to comprise 5 register or bistable stages S1–S5 with inputs 1–5 respectively. Any stage S when set provides a high level on its M output line and the other stages are automatically reset. For example, when input 1 goes high for mode 1 operation S1 is set and line M1 goes high while S2–S5 are reset and lines M2–M5 are low. On the other hand, when input 2 is driven high to set stages S2, M2 goes high and S1 and S3–S5 are reset and lines M1 and M3–M5 are low. The additional circuitry for the automatic mode selection consists of five timers 101–105, And gates 111–117, Or gate 119, inverters 121, 122, one shots 125 and 126, gates 128 and 129, and a double pole double throw (DPDT) switch 130 which is manually operable and is shown in FIG. 5. Also, the console 50 is assumed to include five lights L1–L5 (FIG. 3) which are respectively illuminated when the system operates in modes 1–5 respectively, i.e., when lines M1–M5 are high, respectively.

When On-Off switch 52 is turned On to turn on the system, one shot 126 provides a short pulse, which sets S1 thus driving M1 high and the system is in mode 1. When the output of And gate 78 goes high, if it occurs after a period assumed to be sufficiently long for $V_x$ to appear, e.g., 72 minutes, the output of timer 102 which is designated to measure a time interval of 72 minutes from the time the system is turned On by switch 52, is also high. Thus, gate 111 is enabled, turning On Or gate 80, which activates $L_{EOC}$. On the other hand if gate 78 is enabled, i.e., its output goes high, before the output of timer 102 goes high, i.e., before 72 minutes, the output of inverter 121 is high, thus enabling or turning on gate 112, whose high output sets stage S2. Thus, the system is automatically switched to mode 2. While timer 102 is assumed to measure a time interval of 72 minutes from the time the system is turned On by switch 52, each of the other timers is set to measure a different selected time interval.

Similarly, if the output of comparator 83 goes high before a sufficiently long charging period, measured by timer 101, it indicates that switch 24 opened, possibly due to PS 30 being in the shorted state, while the charging current is above 400ma. Thus, the output of inverter 123 goes high, turning On gate 113 which sets S3 and thereby drives the system into mode 3. In this mode gate 74 is enabled to feed $V_{360}$ to power source 62 to thereby lower the charging current to 360ma, below 400ma.

One shot 125 is activated by M3 and at the end of a period sufficient for the current to drop to below 400ma in mode 3, it opens gate 128. If the switch 24 is still open, as indicated by the high output of comparator 83, it indicates that the switch opening is not due to shorted PS 30 but possibly due to the failure of switch 24 in the open state. Thus, gate 114 is enabled and it sets stage S5 to drive the system to mode 5. In this mode the maximum assumed current is only 100ma, thus requiring a relatively long charging period, e.g., 5 hours. It is measured by timer 103. At the end of the measured period for adequate charging in mode 5, gate 116 is enabled which in turn activates Or gate 80.

When the system is in either modes 1 or 2 gate 129 is open by Or gate 119. Timer 105 measures the approximate expected charging period, e.g., 120 minutes, when the charging current is 600ma in either modes 1 or 2. If at the end of this period Or gate 80 has not been activated it is probably due to the failure of both PS 30 and SE 35 in the open state. Thus, the output of inverter 122 goes high. Therefore, And gate 117 is activated and since gate 129 is open and switch 130 is shown in FIG. 5, the high output of gate 117 sets stage S4, thus driving the system to mode 4. Also, the high output of gate 117 sets flip flop 135, so that in the shown position of switch 130 FF 135, when set, activates Or gate 80.

The switch 130 is in the position as shown when the operator does not know from prior experience during a previous charging operation that the pacer need be charged in mode 4. If, however, this information is known, before turning On switch 52, switch 130 is thrown to the other position from that shown. In the other position switch 130 applies +V to one shot 126 thereby disabling it. Also, +V is applied directly to stage S4 through switch 130. Thus, when switch 52 is turned On, the system is immediately driven to mode 4. In it the charging current is about 280ma (gate 75 is open). After an estimated charging time, e.g., 3 hours, as measured by timer 104, gate 115 activates Or gate 80 through switch 130.

As previously indicated lights L1–L5 may be incorporated in console 50 so that the operator can observe and determine the mode of operation of the system. Whenever Or gate 80 is activated it turns on $L_{EOC}$ which provides the End-of-Charge indication. Also shown in FIG. 5 is a gate 140 connected to the output of comparator 83 and light $L_S$. Gate 140 is enabled only in mode 3 when the current is below 400ma, e.g., 360ma. Thus, any opening of switch 24 except for battery failure in the high impedance state can only be due to the switch 24 having failed in the open state. If indeed such failure occurred the output of comparator 83 is high since the current with switch 24 open will not be 360ma but rather considerably less than 150ma. With the output of comparator 83 high and gate 140 enabled light $L_S$ is energized and turns On to indicate switch 24 failure in the open state.

It should be pointed out that in mode 3 when the expected charging current is only 360ma, i.e., below 400ma when switch 24 may open due to PS 30, the drop in current below 150ma may be used to indicate that the switch 24 failed in the open state thereby illuminating $L_S$. However, it is also possible that the current drop is due to switch 24 opening due to battery failure in the high impedance state, resulting in $V_B > V_{MAX}$. The type of failure may be distinguished by applying a feedback voltage to power source 62 which ramps up so as to cause a charging current in the pacer to increase from a very low amplitude, e.g., Oma to up to less than 400ma, if switch 24 were closed. If the charging current as indicated by $V_i$ is very low, regardless of the ramping feedback voltage, it indicates that switch 24 failed in the open state. If, however, the charging current first increases as the ramp feedback voltage increases, but at some point before the current reaches 400ma, $V_i$ drops, i.e., the charging current drops, it indicates that the increase charging current, flowing through the battery high impedance caused $V_B$ to increase above $V_{MAX}$ and thereby causing switch 24 to open. Thus, it would indicate battery high impedance failure. It should be appreciated that since the actual impedance of the failed battery may vary the charging current which will cause $V_B \gtrsim V_{MAX}$ will vary.

Again it should be stressed that if desired high impedance battery failure, which causes $V_B \gtrsim V_{MAX}$, may be indicated by transmitting a separate signal to external unit 20. As previously indicated this can be accomplished quite conveniently by utilizing the output of comparator 49 (FIG. 2) to turn On a separate oscillator (like oscillator B) rather than cause switch 24 to open. The separate oscillator will transmit a signal at a selected fixed frequency, which when picked up by a separate external coil and a receiver in unit 20 will produce a specific voltage. Such a voltage may be used to provide an indication that the battery 12 failed in the high-impedance state.

From the foregoing it is thus seen that in the tissue stimulation system of the present invention the implanted pacer incorporates battery-protection devices, such as switch 24, PS 30 and SE 35 which are used in monitoring the charging current applied to the battery, it state of charge and any failure thereof. Signals are transmitted to the external unit 20 of the system wherein the charging current is monitored and controlled by controlling the power transmitted to the pacer for battery charging. The external unit is operable in any one of several modes so that when one or more of the protection devices fail, such failure is detected. Based on the detected failure, a mode is selected to enable the charging of the battery in spite of the failure or failures. Mode selection may be achieved either manually or automatically.

In practice, it is highly desirable that the implanted pacer be as small as possible. Thus, it is desirable to reduce the number of protection devices which are included in the pacer to the minimum needed to protect the battery. Hereinbefore the invention was described in connection with an embodiment in which the protection devices include PS 30 and SE 35. Both of these devices in a sense monitor the same battery condition, i.e., its state of charge. The pressure switch 30 acts as a backup protection device in case the signal electrode 35 fails, since the former is assumed to provide an indication of the state of charge which is higher than that which the signal electrode 35 is designed to indicate. Such redundancy is needed only if either device cannot be relied upon to function properly for the expected life of the implanted pacer. If, however, either of these protection devices can be relied upon to operate properly during the pacer's expected life, only one of the state-of-charge sensing devices may be used.

As to switch 24 it is shown in FIG. 1 as a mechanical switch. However, as previously pointed out in practice it is a solid-state device, e.g., a transistor. At present, highly reliable transistors are available which are capable of conducting currents of several amperes which is considerably more than the optimal charging current assumed hereinbefore to be 600ma, or any higher reasonable charging current for an implanted rechargeable battery. Thus, the likelihood of the failure of switch 24 is very remote. Therefore, if desired the system can be designed in which switch 24 is assumed to be fail-proof. In such a system mode 5 can be eliminated.

Likewise mode 4 may be eliminated if the probability that both devices PS 30 and SE 35, which effectively monitor the battery state of charge, will fail in the same state, the open state during the pacer's life expectancy is so small as to be safely ruled out. Thus, if desired, the system may be reduced to a three mode system. Clearly, however, if fewer or more and/or different battery protection devices than those described are implanted, the system may include different and/or more than 5 modes of operation.

Furthermore, any devices capable of sensing the battery state of charge may be used, and are not limited to PS 30 and/or SE 35. For example, temperature sensors which sense battery temperature as a function of battery state of charge may be used. Furthermore, if desired the switch 24 may be opened by a sensing device such as PS 30 when the state of charge is less than full (1C), e.g., 0.85C, while $V_x$ may be produced when full charge is reached. That is, the output of SE 35 may be used to open switch 24, while the output of PS 30 may be transmitted to the external unit 20. Also, in each of the embodiments, shown in FIGS. 4 and 5, the End-of-Charge command is provided when the output of Or gate 80 goes high thereby illuminating $L_{EOC}$. If desired, the output of Or gate 80 may be supplied to the charge power source 62, so that when the output of Or gate 80 goes high, the charge power source 62 is disabled, thereby automatically terminating the supply of charging power.

In practice, highly reliable protection devices are used, to reduce the chance of their failure. Although the likelihood that more than one of them will fail during the pacer's life is quite remote it cannot be ruled out. Since a patient's life may, and often does, depend on the proper operation of the pacer a proper stimulation system has to be operable so as to properly charge and protect the battery, even though more than one protection device failed. This is clearly achievable with the present invention, as hereinbefore described.

The present invention, though not limited to, is primarily directed to a system in which fast battery charging can take place. As previously pointed out the nominal charging current was assumed to be about 600ma. Thus, a 1000mah battery even if it were nearly fully discharged, which in practice will never occur, can be recharged to nearly full charge, e.g., 85% to 100% of full charge in less than 1¾ hours. It is clear however that since the patient's life depends on the proper operation of the pacer, the battery is not permitted to be discharged below a charge level, needed to insure the proper energization of the pulse generator 14.

It has been established that with a properly charged battery of about 1000mah a pulse generator can operate quite safely for a period of several months between charging operations. For example, when a demand inhibited pulse generator is used in the implanted pacer as generator 14, under normal operating conditions the interval between charging operations may be on the order of 6 months.

Although the external unit 20 may be supplied to and controlled by the patient, preferably it is intended to be used in a doctor's office with the patient coming periodically to the doctor's office for battery recharging. Under such conditions and assuming that the pulse generator is of the demand inhibited type the novel system of the present invention can be used as an aid for diagnostic purposes. As is appreciated a demand inhibited type pulse generator generates pulses only when the tissue to be stimulated, e.g., the heart, does not generate the appropriate pulses. If however, the tissue does not produce an appropriate pulse the generator produces a pulse. Thus, the power drainage on the battery depends on the number of pulses which the generator has to produce. If the stimulated tissue condition deteriorates the generator produces pulses more frequently.

Let it be assumed that the patient comes to the doctor's office at regular intervals for battery recharging, and that each recharging operation lasts about an equal duration. This indicates that no deterioration took place in the stimulated tissue between charging operations, since the drainage on the battery is relatively constant. If, however, after one or more charging operations of substantially constant duration, a subsequent operation of recharging the battery to the same level to which the battery was charged on prior occasions lasts longer, it indicates that greater battery drainage occurred since the last charging operation. The most likely reason for the increased battery drainage is increased failure of the stimulated tissue, which caused the generator to produce more pulses than those produced between prior charging operations.

Since with the system of the present invention the time between required charging operations is relatively long, e.g., 6 months or more, a patient may forget to come to the doctor's office for battery recharging, in spite of written or oral reminders. It is therefore desirable to alert the patient when the battery discharges to a state close to a state of charge which may be insufficient to properly energize the pulse generator.

As is appreciated the voltage across a battery depends on its state of charge. Generally, the voltage across a battery is equal or close to its voltage rating, as long as the battery state of charge is above a reasonable state. In practice, the voltage drops very gradually by a small amount as the battery is being drained. However, when the state of charge becomes quite low the voltage drop decreases at a higher rate as the battery is being drained.

In accordance with the present invention the voltage $V_B$ across the battery is monitored and compared with a reference voltage $V_C$. When $V_B \leq V_C$ it indicates that the battery has been discharged (drained) to a low level and that recharging is required. This indication is used to reduce the rate of pulses provided by the pulse generator 14. The reduction in the pulse rate is intended to cause some patient discomfort which the patient is not likely to ignore. Thus, the patient will go to have the battery recharged. For example, assuming that the pulse generator is one used to stimulate the patient's heart, i.e., the implanted pacer is a cardiac pacer, the pulse rate may be decreased from a normal rate, e.g., 72ppm to 60ppm. Such a reduction though not endangering the patient's life, will result in the patient feeling somewhat weaker and therefore it will in all likelihood urge him to see his doctor.

Figure 6:
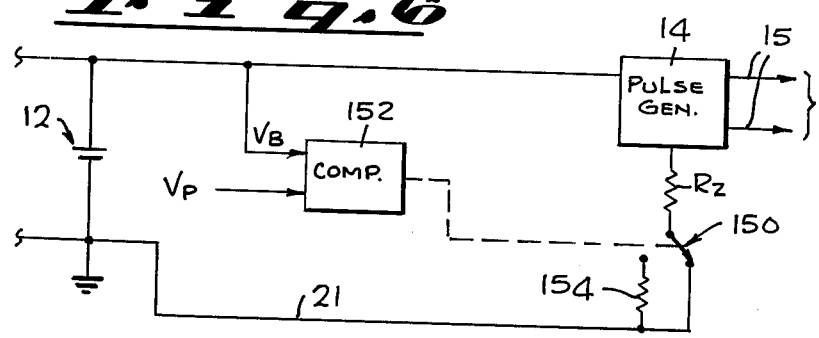
FIG. 6 is a simplified diagram, useful in explaining another feature of the present invention.

It is appreciated that various arrangements may be used to modify the pulse rate of a pulse generator. For example, in the pulse generator particularly shown in FIG. 1A of U.S. Pat. No. 3,888,260, the pulse rate may be decreased by inserting a resistor in series between resistor 42 and line 46A. Similarly, in the pulse generator shown in U.S. Pat. No. 3,942,535, the pulse rate may be changed by increasing the resistance between the base of Q11 and line 52 shown in FIG. 3. The pulse rate change may be achieved by an arrangement as shown in FIG. 6. Therein the pulse generator 14 is shown in block form except that a resistor $R_z$ which is assumed to control the pulse rate is shown external to the block 14. In accordance with the invention, the resistor $R_z$ is shown connected to a reference potential, e.g., ground (line 21) through a switch 150, shown for explanatory purposes as a mechanical switch. In the position as shown $R_z$ is connected to ground through the switch 150. A comparator 152 is also included. It compares $V_B$ with $V_P$ and when $VB \leq V_P$ the output of comparator 152 is assumed to go high driving switch 150 to its other position, in which resistor $R_z$ is connected to ground through a resistor 154. Thus, the pulse rate provided by the pulse generator decreases.

It should be pointed out that the circuitry just described is intended to indicate to the patient that the battery has reached a low state-of-charge, i.e., the circuitry effectively provides a battery low state-of-charge indicator. This is achieved by causing a sensation in the body, e.g., some patient discomfort, of course without endangering the patient's life. Hereinbefore it was assumed that this is achieved by lowering the rate of pulses provided by the pulse generator. Depending on the particular implanted pacer and the tissue which is stimulated, a method other than lowering the pulse rate may be used to provide the battery low state-of-charge indication. For example, instead of reducing the pulse rate it may be increased to cause some body discomfort or sensation without endangering the patient's life.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. A rechargeable tissue stimulation system adapted to be in part implanted in the body of a patient for applying electrical stimulation pulses to selected body tissue comprising:

implanted pulse circuit means for generating and applying said stimulation pulses;

implanted rechargeable battery means operably connected to supply operating energy to said pulse circuit means;

implanted means including at least first sensing means coupled to said battery means for sensing the state-of-charge of said battery means and for transmitting a first signal when the state-of-charge of said battery means reaches a first level;

external means including an external source for providing recharging energy; and implanted recharge means responsive to recharging energy provided by said external source for recharging said battery means, means for generating and transmitting a signal indicative of the rate said recharge means recharge said battery means, said external means including receiver means for receiving said first signal and the signal indicative of the rate said battery means is recharged, and external circuit means responsive to the signals received by said receiver means for controlling the energy supplied by said source.

2. The system as described in claim 1 wherein said implanted means further includes second sensing means coupled to said battery means for providing a second signal when the state-of-charge of said battery means reaches a second level and further including control means responsive to the second signal from said second sensing means and the signal indicative of the rate said battery means is recharged for limiting the rate at which said battery means is recharged not to exceed a preselected rate.

3. The system as described in claim 2 wherein said first sensing means provide said first signal when said battery means is recharged to a said first level which is lower than the second level of the state-of-charge of the battery means when said second sensing means provide said second signal, said control means including means for maintaining the limit on the rate at which said battery means is charged, once said rate has been limited as long as said recharged means receive energy from said external power source.

4. The system as described in claim 3 wherein said external means include means for providing an indication when the first signal is received by said external receiver means to indicate that said battery means has been recharged to said first level of said state-of-charge.

5. The system as described in claim 1 wherein said implanted means further includes second sensing means coupled to said battery means for providing a second signal when the state-of-charge of said battery means reaches a second level and further including control means responsive to the second signal from said second sensing means and the signal indicative of the rate said battery means is recharged for limiting the rate at which said battery means is recharged not to exceed a preselected rate which is greater than zero, said control means including means for maintaining the limit on the rate at which said battery means is charged, once said rate has been limited as long as said recharge means receive energy from said external power source.

6. The system as described in claim 5 wherein said external circuit means include means for providing $n$ external reference signals, where $n$ is an integer not less than 1, and means for selectively controlling the energy provided by said source as a function of either one of said $n$ external reference signals or the received signal indicative of the rate said battery means is recharged.

7. The system as described in claim 5 wherein said control means include means responsive to the signal indicative of the rate said battery means are recharged for limiting the rate of charge of said battery means to said preselected rate, after said rate first exceeded a selected maximum rate for a predetermined time period.

8. The system as described in claim 7 wherein the external means include circuit means for providing $n$ external reference signals, where $n$ is an integer not less than 1, and means for selectively controlling the energy provided by said external source as a function of either one of said $n$ external reference signals or the received signal, indicative of the rate said battery means is recharged.

9. The system as described in claim 8 wherein said implanted means include third sensing means for providing a third signal when said battery means is charged to a third level, greater than said second level, and said control means being responsive to said third signal for limiting the rate of charge of said battery means to said preselected rate after receiving said third signal and for thereafter maintaining the rate of charge at said preselected limit as long as said recharge means receive energy from said external source.

10. The system as described in claim 5 wherein said implanted means include third sensing means for providing a third signal when said battery means is charged to a third level, greater than said second level, and said control means being responsive to said third signal for limiting the rate of charge of said battery means to said preselected rate after receiving said third signal, and for limiting said rate of charge as long as said recharge means receive energy from said external source.

11. A rechargeable system adapted to be in part implanted in a patient, comprising:
implanted circuit means for performing a selected function in the patient's body:
an implanted rechargeable battery for powering said circuit means:
external means including an external power source for providing recharging energy:
implanted recharge means responsive to energy from said external power source for providing a recharging current to said battery:
first charge sensing means for providing a first signal when the state-of-charge of said battery is not less than a first charge level;
current sensing means for providing a signal indicative of the current amplitude which is supplied by said recharge means to said battery; and
recharge control means coupled to said recharge means to said first charge sensing means and to said current sensing means for controlling the recharging current which can be supplied to said battery from said recharge means, said recharge control means include means for limiting the current not to exceed a selected low level, once the current sensing means provide said signal, definable as the current-amplitude-indicating signal, which indicates that the recharge current is not less than a first level, and said sensing means provide said first signal as long as the recharge means receive energy from said external power source which is above a selected low energy level.

12. The system as described in claim 11 wherein said system further includes first transmitting means for transmitting said current-amplitude-indicating signal to the body exterior, and said external means include receiver means for receiving said transmitted signal, $n$ sources of $n$ different reference signals, where $n$ is an integer not less than 1, and power source control means for selectively controlling the external power source to provide energy at a level which is a function of either said current-amplitude-indicating signal or one of said $n$ reference signals.

13. The system as described in claim 11 wherein said recharge control means include switch means, switchable between a first state in which said switch means provide a low resistance path between said recharge means and said battery and a second state in which said switch means provide a high resistance path between said recharge means and said battery to limit the charging current not to exceed said selected low level, said recharge control means being responsive to the first charge signal from said first sensing means and the current-amplitude-indicating signal when the latter indicates a charging current which is not less than said first level, for switching said switch means to said second state, said switch means remaining in said second state as long as said recharging means receive energy from said source, and said system further includes first transmitting means for transmitting said current-amplitude-indicating signal to the exterior of the body, and external receiver means for receiving said current-amplitude-indicating signal.

14. The system as described in claim 13 wherein said recharge control means further includes means for switching said switch means to said second state when the current-amplitude-indicating signal indicates that the recharging current is not less than a second level, higher than said first level, for a preselected time interval, said switch means remaining in said second state as long as energy is received by said recharge means.

15. The system as described in claim 14 further including second charge sensing means for providing a second signal when the state-of-charge of said battery reaches a second charge level, which is higher than said first charge level, and said recharge control means being responsive to said second signal for switching said switch means to said second state.

16. The system as described in claim 14 wherein said external means include receiver means for receiving the current-amplitude-indicating signal, means for providing $n$ different reference signals and mode select means for controlling said power source to provide energy as a function of either the received signal or one of said $n$ reference signals.

* * * * *